(12) United States Patent
Aesaert et al.

(10) Patent No.: US 11,337,359 B2
(45) Date of Patent: May 24, 2022

(54) GROUND BEARING CAPACITY

(71) Applicant: CNH Industrial America LLC, New Holland, PA (US)

(72) Inventors: Glenn Aesaert, Izegem (BE); Christopher A. Foster, Mohnton, PA (US); Bart M. A. Missotten, Herent (BE); John H. Posselius, Ephrata, PA (US)

(73) Assignee: CNH Industrial America LLC, New Holland, PA (US)

( * ) Notice: Subject to any disclaimer, the term of this patent is extended or adjusted under 35 U.S.C. 154(b) by 230 days.

(21) Appl. No.: 16/618,702

(22) PCT Filed: Jun. 1, 2018

(86) PCT No.: PCT/EP2018/064426
§ 371 (c)(1),
(2) Date: Dec. 2, 2019

(87) PCT Pub. No.: WO2018/220159
PCT Pub. Date: Dec. 6, 2018

(65) Prior Publication Data
US 2020/0093054 A1    Mar. 26, 2020

(30) Foreign Application Priority Data

Jun. 2, 2017  (BE) .................................. 2017/5397

(51) Int. Cl.
*A01B 79/00* (2006.01)
*A01D 41/127* (2006.01)
(Continued)

(52) U.S. Cl.
CPC .......... *A01B 79/005* (2013.01); *A01D 41/127* (2013.01); *G01B 21/32* (2013.01);
(Continued)

(58) Field of Classification Search
CPC ............... A01B 79/005; A01D 41/127; A01D 41/1274; G01B 21/32; G01N 33/24;
(Continued)

(56) References Cited

U.S. PATENT DOCUMENTS 5,673,637 A    10/1997  Colburn, Jr. et al.
6,029,106 A *  2/2000  Hale ................... A01B 79/005
                                                    342/357.52
(Continued)

FOREIGN PATENT DOCUMENTS

EP    0504913 A1    9/1992
EP    2508057 A1    10/2012

OTHER PUBLICATIONS

PCT International Search Report for PCT application PCT/EP2018/064426, dated Sep. 10, 2018 (14 pages).
(Continued)

*Primary Examiner* — Michael J Zanelli
(74) *Attorney, Agent, or Firm* — Peter Zacharias; Patrick Sheldrake

(57) ABSTRACT

A combine harvester comprising a controller, at least one first sensor adapted to measure a first parameter related to soil deformation, and at least one second sensor adapted to measure a second parameter related to wheel slip. The first sensor is adapted to provide a first output to the controller. The second sensor is adapted to provide a second output to the controller. The controller is configured to determine a ground bearing capacity based on a combination of the first output and the second output.

11 Claims, 3 Drawing Sheets

(51) Int. Cl.
*G01B 21/32* (2006.01)
*G01N 33/24* (2006.01)
*G05D 1/02* (2020.01)

(52) U.S. Cl.
CPC ........... *G01N 33/24* (2013.01); *G05D 1/0227* (2013.01); *G05D 2201/0201* (2013.01)

(58) Field of Classification Search
CPC ........ G05D 1/0227; G05D 2201/0201; B60W 2300/158
See application file for complete search history.

(56) References Cited

U.S. PATENT DOCUMENTS

| | | | |
|---|---|---|---|
| 6,061,618 A * | 5/2000 | Hale | A01B 79/005 342/357.52 |
| 6,484,652 B1 | 11/2002 | Colburn, Jr. | |
| 2006/0243511 A1 | 11/2006 | Ho et al. | |
| 2009/0173147 A1 * | 7/2009 | Sandomirsky | E02D 1/022 73/84 |
| 2010/0107584 A1 | 5/2010 | Sheidler et al. | |
| 2012/0323452 A1 * | 12/2012 | Green | A01B 69/008 701/50 |
| 2017/0101103 A1 | 4/2017 | Foster et al. | |
| 2019/0360165 A1 * | 11/2019 | Nilsson | G01C 21/20 |

OTHER PUBLICATIONS

On-the-Go Soil Data Collection Map-based Application Solo Surveyor/Solo with ESP Sensing, Soil Doctor® Systems, last accessed Feb. 21, 2017, 2 pages.

Soil Doctor® System Provides Combine Soil Mapping & Synchronized Yield Analysis, dated Nov. 26, 2001, 7 pages.

* cited by examiner

GROUND BEARING CAPACITY

BACKGROUND OF THE INVENTION

The present invention relates to a combine provided with multiple sensors.

During harvesting, combines are typically the first vehicles to be driven over a field to be harvested. When the combine has passed over part of the field, further agricultural vehicles can be driven over this part of the field for various reasons. The further agricultural vehicles are for example tractors with large storage trailers for unloading harvested crop from the combine. The combine is typically provided with a storage tank for storing at least a part of the harvest. The storage tank of the combine is however not sufficient to store the complete harvest. Therefor the combine storage tank is periodically emptied into an external storage tank pulled by a tractor. These vehicles drive over the parts of the field that have been harvested by the combine.

With machines becoming larger and larger, operators of combine harvesters as well as operators of further agricultural vehicles driving over the harvested parts of the field have to pay attention not to drive onto weak spots (spots with low ground bearing capacity) of the field, for example wet or sloped spots. Driving onto weak spots could have one or more of the following drawbacks. The first drawback is that the vehicle, the combine harvester or the further agricultural vehicle, could get stuck and cannot get through. The second drawback is that the vehicle could damage the structure of the soil thereby decreasing the yield of the next crop.

It is a first object of the present invention to assist operators of agricultural vehicles to choose or adapt driving routes and/or driving parameters to minimize the above mentioned drawbacks. It is a further object of the present invention to provide relevant input to autonomously driven agricultural vehicles so that such vehicles are less likely to encounter the above mentioned drawbacks.

SUMMARY OF THE INVENTION

To this end, the invention provides a combine comprising at least one first sensor adapted to measure a first parameter related to soil deformation and comprising at least one second sensor adapted to measure a second parameter related to wheel slip, the combine being adapted to provide a first output of the at least one first sensor and a second output of the at least one second sensor to a controller configured to determine a ground bearing capacity based on a combination of the first output and the second output.

The invention is based on the insight that ground bearing capacity is a basis for determining whether any vehicle could be safely driven over a field. The ground bearing capacity is based on two phenomenon's, the first one being the deformation of the soil under the load of the combine and the other one being the resistance of the ground surface against slipping. In determining the ground bearing capacity, the controller can use combine parameters such as weight and size of the wheels in order to relate the deformation and/or slip to the context where these parameters are measured. It is therefore possible to calculate a vehicle independent ground bearing capacity. Using this ground bearing capacity, it can be determined for each vehicle to be driven over the field whether the ground bearing capacity is sufficiently high for the vehicle to get through and/or not to damage the structure of the soil. In this context it will be clear that an agricultural vehicle with a first weight and small wheels will more likely get stuck as a result of soil deformation than a second agricultural vehicle with the same weight having larger and wider wheels.

A further advantage of determining ground bearing capacity based on sensor data from the combine, is that the combine is the first vehicle to drive over a field to be harvested. Therefore, the ground bearing capacity is based on most recent, therefore highly relevant data, in particular from sensors provided at the combine driving over the field while harvesting. The ground bearing capacity is therefore not based solely on historical data. Particularly in wet conditions, historical data might not be accurate to determine a ground bearing capacity. The ground bearing capacity determined by the controller based on the sensor data from the combine is therefore highly useful for operators of agricultural vehicles to avoid getting stuck and/or damaging the structure of the soil.

Preferably the combine comprises a ground drivability module, at least partially incorporating a controller, the ground drivability module being configured to determine combine driving parameters based on the ground bearing capacity determined by the controller. The ground drivability module is provided at the combine to assist the operator of the combine to choose the settings of the combine to improve the drivability. In the context of the present invention drivability of a vehicle is related to avoiding that the vehicle gets stuck and cannot get through, and is related to the vehicle not slipping thereby losing traction and/or driving direction.

The ground drivability module can suggest or adapt speed settings, steering wheel settings, traction related settings, power settings and other driving related settings of the combine. The determined combine driving parameters can be suggested to the operator or can be automatically set on the combine by the ground drivability module, depending on the preferences of the operator and/or the configuration of the ground drivability module.

Preferably the ground drivability module is configured to determine at least one of a risk of the combine getting stuck and a risk of damaging a soil structure, and to adapt the combine driving parameters when the risk exceeds a predetermined threshold. The ground drivability module is preferably configured to automatically adapt the combine driving parameters before the combine gets stuck and/or before the combine damages the soil structure. This improves the drivability of the combine.

Preferably the combine comprises a header with at least one further sensor adapted to measure a further parameter related to a ground bearing capacity, the header being adapted to provide a further output of the at least one further sensor to the controller. The header is provided at a front end of the combine and in front of the front wheels of the combine. Therefore, when the header is provided with sensors adapted to measure a parameter that can be related to the ground bearing capacity, an indication of the ground bearing capacity can be obtained before the front wheels reach that part of ground. This allows the combine to react to a decrease of the ground bearing capacity before the combine gets stuck.

Preferably the at least one further sensor comprises multiple sensors divided over the width of the header so that the further parameter is determined at intermitting distances over substantially the complete width of the header. Soil deformation and wheel slip manifest under the wheels of the combine, so that these parameters can be most easily measured under the tracks of the combine. By providing a further set of sensors over the complete width of the header, a broader and more detailed view can be obtained on the ground bearing capacity. Particularly for further agricultural vehicles, driving over the harvested parts of the field, it is interesting to gather information relating to the ground bearing capacity over the complete width of the header.

Preferably the controller is further configured to recursively calibrate the at least one further sensor based on the determined ground bearing capacity so as to obtain an estimated ground bearing capacity for ground under the header. The ground bearing capacity is determined based on a measurement related to soil deformation and a measurement relating to wheel slip. These measurements are typically directly or indirectly related to effects and reactions of the soil to the wheels of the combine. Therefore, these measurements are only accurate at the location where the wheels touch the ground. By recursively calibrating the ground bearing capacity under the tracks with the sensor data from the header, a ground bearing capacity can be estimated for ground under the header. Particularly, the sensors in the header that are located in line with the tracks of the combine are used to recursively calibrate these sensors based on the measurements of soil deformation and slip on these respective tracks. Such recursive calibration gives an insight in the ground bearing capacity for all the sensors on the header.

Preferably the ground drivability module is configured to adapt combine driving parameters based on the estimated ground bearing capacity. Ground bearing capacity is estimated based on sensors at the header, therefore being able to predict the ground bearing capacity of the ground in front of the combine. This allows the combine to automatically stop when the ground in front of the combine is determined not to be able to carry the combine. In this manner, the combine can be stopped before it gets stuck.

Preferably the further sensor is chosen from a density sensor, a humidity sensor and a conductivity sensor. These sensors can easily be mounted to a header. Furthermore, tests have shown that the output of any of these sensors can be related to the ground bearing capacity.

Preferably the combine comprises at least a third sensor to measure a third parameter relate to a geographical position of the combine, the combine being adapt to provide a third parameter to the controller which controller is further configured to relate the third parameter to the determined ground bearing capacity thereby obtaining a ground bearing capacity mapping. This mapping can be used by further agricultural vehicles driving over the harvested parts of the field to determine optimal routes or paths based on the ground bearing capacity mapping.

Preferably the ground bearing capacity mapping is broadcasted to agricultural vehicles in a proximity of the combine thereby allowing these agricultural vehicles to adapt their driving parameters based on the ground bearing capacity mapping.

Preferably the first sensor is chosen from a header position sensor, a driving power sensor and a pair of density sensors when a first one of the pair is arranged in front of a wheel and a second one of the pair is arranged behind the wheel. Each of these sensors measure a parameter that is related to soil deformation.

Preferably the second sensor is a wheel slip sensor. The wheel slip sensor measures a parameter that is related to the slip of the wheel of the combine.

BRIEF DESCRIPTION OF THE DRAWINGS

Some embodiments of apparatus and/or methods in accordance with embodiments of the present invention are now described, by way of example only, and with reference to the accompanying drawings, in which.

DETAILED DESCRIPTION OF THE DRAWINGS

Figure 1:
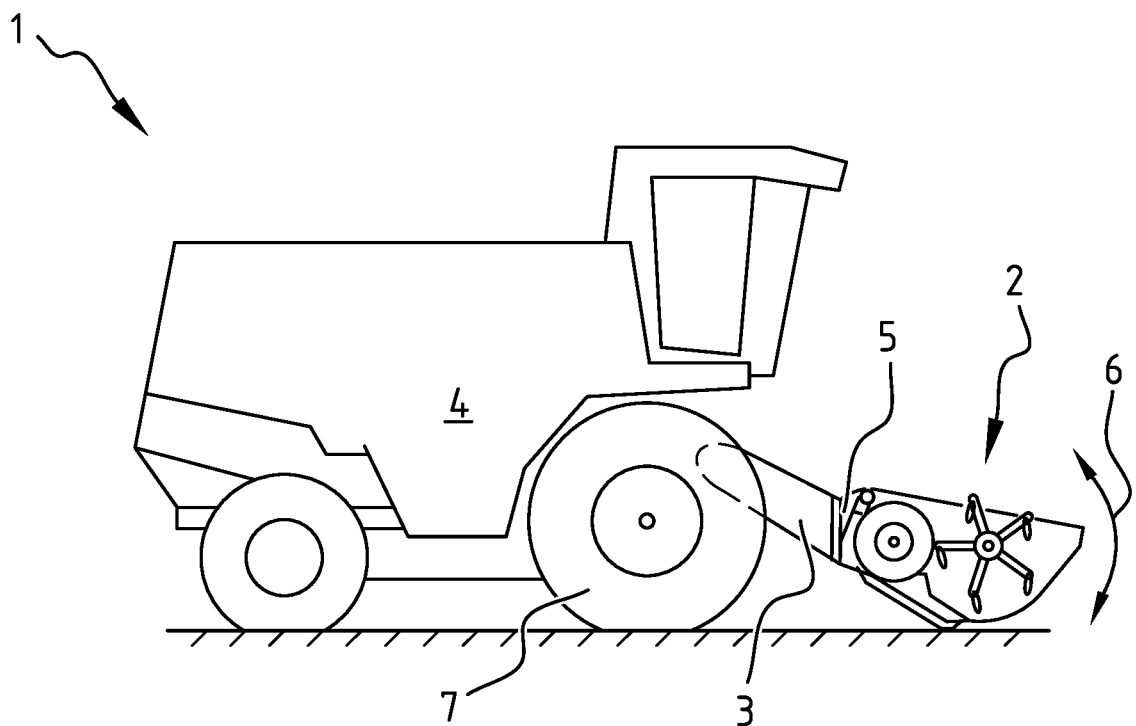
FIG. 1 shows a side view of a combine according to an embodiment of the invention.

FIG. 1 shows a side view of a combine 1. In operation, a header 2 is connected to the combine 1. The combine 1 comprises a feeder 3 which is connected to the header 2 via a header mounting frame 5 provided at the frontal end of the feeder 3, and is provided for taking in harvested crop material from the header 2 towards the body 4 of the combine 1.

The header 2 has to be at a height and has to be positioned in a fore-aft position with respect to the combine 1. Thereby the fore-aft position defines the angle between the cutting knives of the header and the ground surface. The height is determined by the angular position of the feeder 3 with respect to the combine 1. Tests have shown that an ideal fore-aft position depends on the type of crop material to be harvested. Therefore, the fore-aft position is preferably adaptable. Furthermore, tests have shown that an ideal height of the header depends on multiple factors including the type of crop material but also the flatness and rigidity of the ground surface. As an example, in a combine 1 in operation, the majority of the weight is carried by the front wheels 7. In this context, it is noted that wheels should be interpreted broad, preferably as ground engaging means. Therefore the term wheels shall be held to include tracks when the combine 1 is at least partially supported on the ground via for example rubber tracks. When the combine 1 sinks at least partially into the ground surface with its front wheels 7, due to the weight of the combine 1 and header 2, the height of the header is increased to prevent the header 2 from touching the ground surface. Increasing the height of the header 2 can be easily achieved by lifting the header via the feeder 3.

The change of position of the header 2 with respect to the combine 1 is illustrated in FIG. 1 with reference number 6. This position is determined by a combination of the fore-aft position and the height of the header 2. The fore-aft movement is defined as a movement of the header mounting frame 5 with respect to the feeder 3 around an axis which is substantially horizontal and transverse to the forward driving direction of the agricultural vehicle 1. In a preferred embodiment of the present invention, the load on the wheels of the agricultural vehicle is determined, which load may vary by loading/unloading crop material from the agricultural harvester, and a fore-aft compensation movement and/or height compensation movement is automated to obtain the optimal header position in multiple different states of the combine.

The explanation above shows that the position of the header is related to the soil deformation. A rigid soil has as a result that particularly the front wheels 7 of the combine are carried on top of the soil such that the header 2 only needs to be lifted at a minimum height. A deformable soil has as a result that particularly the front wheels 7 of the combine sink into the soil such that the header 2 needs to be lifted significantly higher than the minimum height to not touch the ground surface.

Additionally or alternatively to the position of the header, also power required to reach a predetermined speed with the combine is related to the soil deformation. When the front wheels 7 sink into the soil, drag is significantly higher than when the wheels are carried on top of a rigid soil. The drag is the result of the soil deformation and/or displacement of soil when the wheels move over the field. The soil displacement is as a result of the deformation and the sinking of the wheels 7. Therefore the power required by the combine 1 to maintain or reach a predetermined speed is related to the soil deformation.

When soil deformation increases, for example as a result of the weight of the combine in combination with soil humidity and/or soil structure, several drawbacks may occur. A first drawback relates to the yield of the field. The soil can be deformed by a combine to such an extent that the soil can be considered damaged. A damaged soil is defined as a soil wherein the next seasons yield is decreased compared to an expected yield without damage. In this context, it is noted that a soil can be deformed without affecting the soil's structure. Such deformation is generally not considered as damage to the soil. However when the soil structure changes as a result of the deformation, yield is likely to decrease so that soil can be considered damaged. A second drawback relates to the combine getting stuck on the field. When the soil deforms, and the resistance against movement increases above a predetermined threshold, a situation may occur wherein the combine cannot move forward nor move backwards. Such a situation is to be avoided.

Besides soil deformation, another phenomenon can significantly hinder driving an agricultural vehicle over the field to such extent that the vehicle gets stuck. This phenomenon relates to wheel slip. Particularly when the soil is slippery and sloped, an agricultural vehicle can get stuck on a field. It is noted that wheel slip could be independent from soil deformation. A very hard and slippery soil could show very little deformation and yet show a high risk of wheel slip.

Embodiments of the invention are based on the insight that both soil deformation and wheel slip determine the drivability of the vehicle on the soil. In this context, drivability relates to the ease of driving the vehicle along a predetermined path, including maintaining the vehicle on the predetermined path and including the vehicle not getting stuck on the path.

In the description, the term ground bearing capacity is used. Based on the above, it is clear that the ground bearing capacity relates to the capability of the soil of carrying a certain weight without excessive deformation. The ground bearing capacity is determined based on both soil deformation parameters and wheel slip parameters. Thereby in calculating a ground bearing capacity, preferably account is taken of the context of the sensor data relating to soil deformation and/or relating to wheel slip. In particular, when soil deformation is measured at a combine, the weight of the combine, as well as the size of the wheels of the combine and optionally further parameters and/or properties of the combine are taken into account when calculating a ground bearing capacity. In this manner, a ground bearing capacity can be calculated that is vehicle independent. For the soil deformation, the ground bearing capacity could comprise a value relating to a deformation in function of a predetermined force. The ground bearing capacity could be a set of values, and is preferably a single value, that can be used to calculate the drivability of an agricultural vehicle on the ground. Thereby, preferably a field is segmented and a ground bearing capacity value is calculated for each segment of the field.

Figure 2:
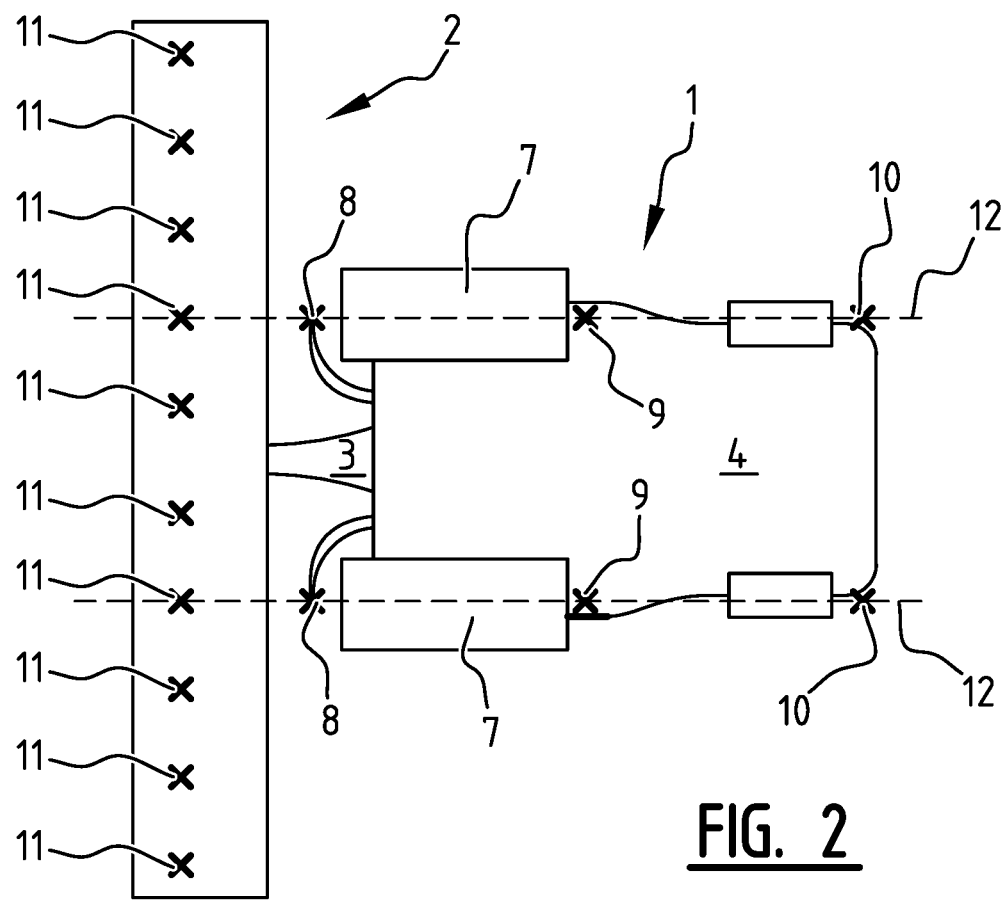
FIG. 2 illustrates a schematic top view of a combine according to an embodiment of the invention.

FIG. 2 shows a schematic top view of a combine 1 with a header 2. The header 2 is connected to a body 4 of the combine 1 via the feeder 3. In operation, the front wheels 7 carry a majority of the weight of the combine and header. In the figure, locations for sensors are schematically indicated at the combine 1 and header 2.

A first soil sensor 8 is preferably provided before the front wheels 7 of the combine 1. Further preferably, a first soil sensor 8 is placed in front of each one of the front wheels 7. A soil sensor is preferably a density sensor. The soil sensor may also be a humidity sensor and/or a conductivity sensor. Each of these sensors are adapted to measure a soil parameter.

A second soil sensor 9 is preferably provided behind the front wheels 7. Preferably the second soil sensor is the same type of sensor as the first soil sensor 8. This allows to compare measurements of the second soil sensor 9 with measurements of the first sensor 8. When the combine 1 moves forward over a field, the difference between the second soil sensor 9 measurement and the first soil sensor 8 measurement can be directly related to the effect of the wheel 7 on the soil for the measured parameter. For example when the first soil sensor 8 measures a first density value and the second soil sensor 9 measures a second density value that is substantially the same as the first density value, then it may be concluded that the passing of the wheel 7 only has a minor effect on the density of the soil. It will be clear to the skilled person that preferably measurements of the same field spot are compared, so that there is a time difference between the measurement of the first sensor 8 and the second sensor 9 which time difference depends on the speed of the combine.

These soil sensors 8 and 9, and in particular the difference between the values measured by the first and second soil sensors 8 and 9 can be related to the soil deformation. As explained above, other combine parameters such as header position and/or power, which can be measured directly or indirectly via a sensor, can also be related to the soil deformation.

In FIG. 2, a third soil sensor 10 is provided behind the rear wheels of the combine. This third soil sensor could be provided instead of the second soil sensor 9 or can be provided additionally to the first and second soil sensors 8 and 9. The third soil sensor 10 can operate together with the first and/or second soil sensor 8, 9 in the same manner as is described above in relation to the first and second soil sensors 8 and 9.

FIG. 2 further shows that the header 2 is provided with multiple fourth soil sensors 11. The fourth soil sensors are preferably distributed over the width of the header 2 to cover substantially the complete width of the header. Furthermore, at least one of the multiple forward soil sensors 11 is located substantially in line with the front wheels 7 of the combine 1. In FIG. 2, two sensors are located in line with the front wheels 7.

In FIG. 2 the tracks of the combine 1 are indicated with reference number 12. All sensors provided on or near the track 12 can measure a same spot of the soil when the combine 1 moves forward over the field. This allows to recursively calibrate the measurement of the fourth soil sensors 11 based on further measurements of the first soil sensor 8, the second soil sensor 9 and/or the third soil sensor 10. Based on this recursive calibration of the fourth sensors that are located on the tracks 12, other ones of the fourth sensors are also calibrated. Even without the presence of first soil sensor 8 and second soil sensor 9 and third soil sensor 10, such recursive calibration can be implemented based on for example soil deformation measurements and/or wheel slip measurements on the combine 1. Since the soil deformation manifests under the wheels of the combine 4, a fourth soil sensor 11 in line with the wheel 7 can be calibrated.

Providing multiple soil sensors on the header has two main advantages. A first main advantage relates to the measurement being done before the wheels of the combine 1 arrive at that part of the soil. This allows to detect a trend of improving or worsening of soil conditions using soil deformation measurements on the wheels of the combine 1, and estimating a future evolution based on the fourth soil sensor. In other words, the ground bearing capacity can be estimated and predicted so that based on this estimation the combine can be controlled. Combine driving parameters are adapted to increase the drivability despite the ground bearing capacity. In an extreme example, the combine can be stopped before getting stuck. A second advantage relates to the header 2 covering a larger part of the field than the combine 1. By distributing the multiple fourth soil sensors 11 over the complete width of the header, the ground bearing capacity can be determined over this complete width, instead of only on the tracks 12. This allows to create a mapping of the field such that ground bearing capacity is available in more detail and for substantially the complete field.

Figure 3:
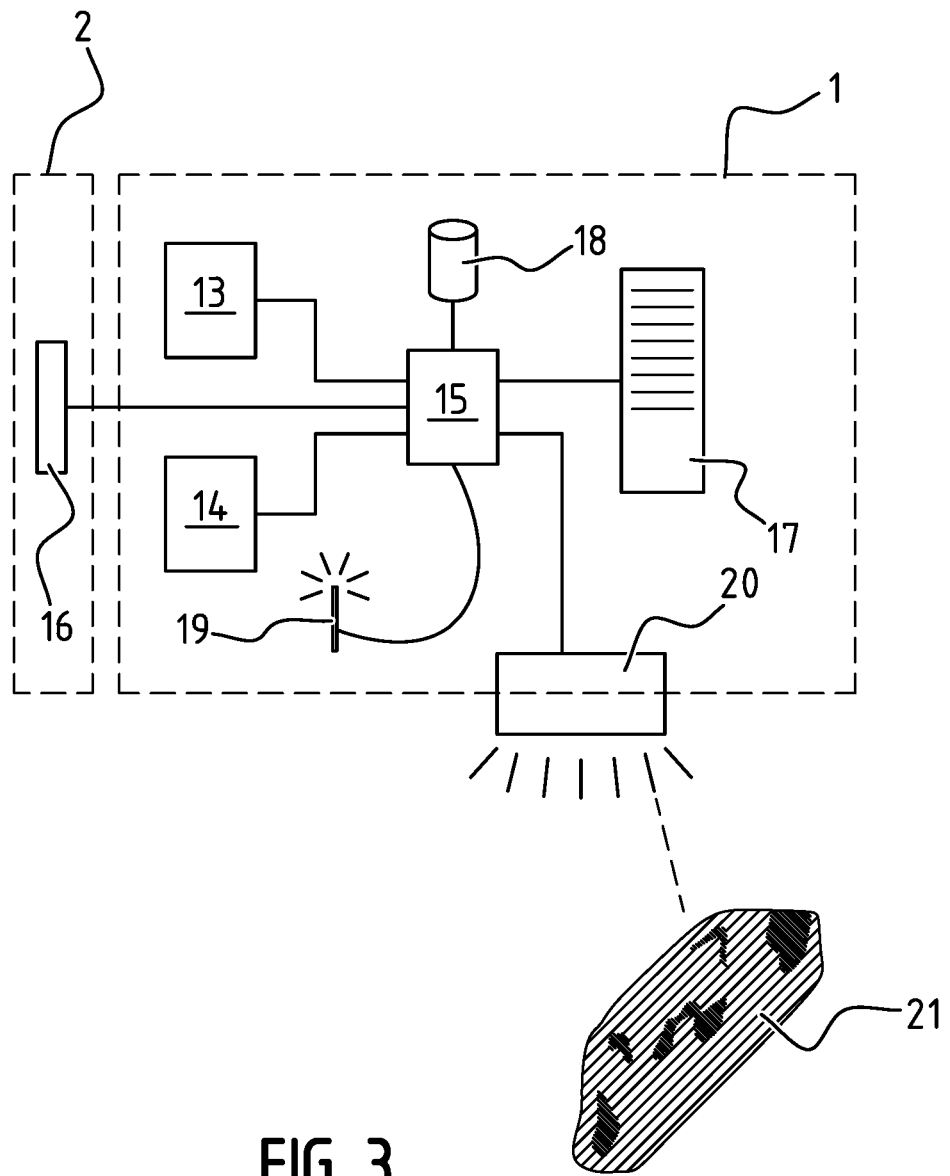
FIG. 3 shows a scheme of a combine according to a first embodiment of the invention.

FIG. 3 schematically illustrates a first embodiment of the invention. In particular FIG. 3 illustrates how sensor data is collected, transmitted and used to reduce the risk of agricultural vehicles getting stuck and to reduce the risk of damaging the soil. In the embodiment of FIG. 3 at least one first sensor 13 is provided to measure a parameter that is related to soil deformation. The description above makes clear that this at least one first sensor could be formed by a position sensor of the header 2, by a power sensor to measure the power that is needed to maintain a certain speed, and/or by a first, second and/or third soil sensor 8, 9, 10. The skilled person will recognize that other sensors can be used to measure parameters that are related directly or indirectly to the soil deformation.

The combine 1 further comprises at least one second sensor 14, the at least one second sensor 14 is adapted to measure a parameter related to wheel slip. The skilled person will recognize that such at least one second sensor 14 can be formed by wheel rotation sensors, but also by soil humidity sensors and/or by slope sensors.

The header 2 comprises at least one further sensor 16. The at least one further sensor 16 of FIG. 3 is preferably formed by the multiple fourth soil sensors 11 which are shown in FIG. 2. The agricultural vehicle 1 further comprises a position sensor 19. Each of these sensors 13, 14, 16 and 19 are provided to output their data to a ground drivability module 15. In the embodiment of FIG. 3 the ground drivability module includes a controller which is adapted to calculate a ground bearing capacity based on the sensor data received at the module 15. While calculating the ground bearing capacity, the controller in the ground drivability module 15 can use data and/or parameters saved in a database 18 and relating to parameters and/or properties of the combine 1. In this context, it is noted that a controller is defined as a combination of software and/or hardware components. In the same way, a module is defined as a combination of software and/or hardware components. Both a controller and a module can therefore be distributed over multiple physical entities.

The ground drivability module 15 is preferably adapted to calculate combine driving parameters 17 to optimize the driving of the combine taking account of the ground bearing capacity. In an extreme situation, these driving parameters comprise a stop-action to prevent the combine from getting stuck. Other driving parameters might relate to driving speed, position of the steering wheels and other parameters. As an example, when the ground bearing capacity is low, the combine driving parameters 17 might suggest to the operator to only use half of the crop storage tank of the combine 1 to keep the weight of the combine 1 as low as possible.

By relating the position sensor output 19 to the calculated ground bearing capacity, the ground drivability module 15 can create a ground bearing capacity mapping. Such mapping is preferably communicated to other vehicles via a communication module 20. In FIG. 3, communication module 20 broadcasts a ground bearing capacity mapping 21. In the example of FIG. 3 the ground bearing capacity mapping 21 shows a part of the field wherein segments are colored to indicate the different ground bearing capacity on that segment of the field.

Figure 4:
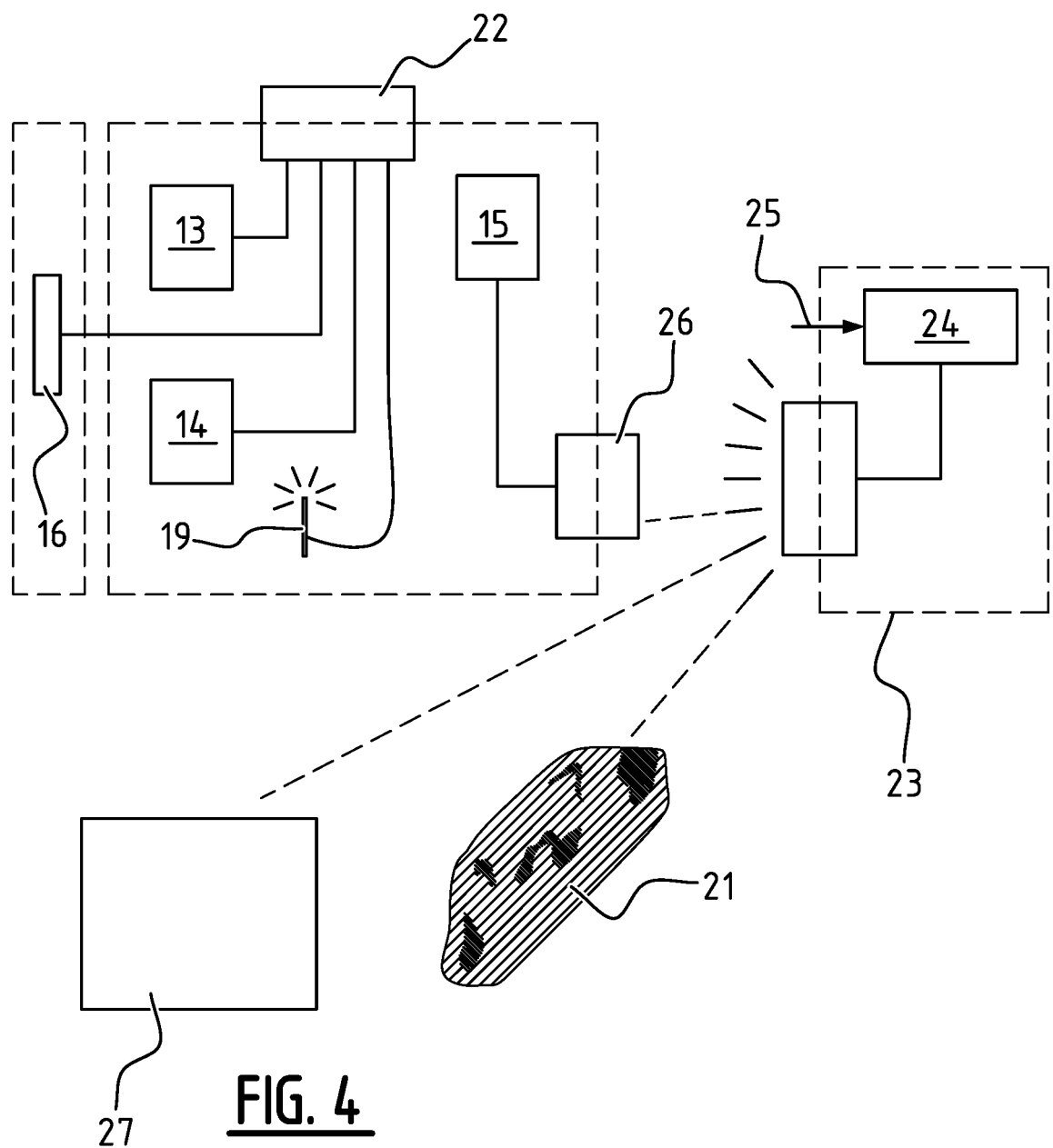
FIG. 4 shows a scheme of a combine according to a second embodiment of the invention.

FIG. 4 shows an alternative embodiment of the invention. The embodiment of FIG. 4 corresponds to the embodiment of FIG. 3 by the combine 1 having the at least one first sensor 13, the at least one second sensor 14, the position sensor 19 and by having, at the header 2, at least one further sensor. The embodiment of FIG. 4 further corresponds to the embodiment of FIG. 3 in that each of these sensors 13, 14, 19, 16 are adapted to output their data to a controller. However the embodiment of FIG. 4 distinguishes by the controller 24 being located on a remote server 23. Thus the sensor data is transmitted via a transmission module 22 to the server 23. At the server 23, the controller 24 processes the sensor data to calculate a ground bearing capacity. Using the position sensors 19, a ground bearing capacity mapping 21 can be calculated similar to the ground bearing capacity mapping 21 in the embodiment of FIG. 3.

The server 23 broadcasts the ground bearing capacity mapping 21 to the agricultural vehicle 1. The agricultural vehicle 1 receives the ground bearing capacity mapping 21 via a receiving module 26. The agricultural vehicle can use this ground bearing capacity mapping 21 in a ground drivability module to calculate driving parameters similar to the embodiment of FIG. 3. The ground bearing capacity mapping 21 is preferably also broadcasted to further agricultural vehicles 27 to allow these vehicles to be navigated over the field taking into account the ground bearing capacity. In practice, an agricultural vehicle can be navigated over a field along a path that is determined to lay around segments having low ground bearing capacity. This increases the efficiency of the agricultural vehicle and reduces the risk of the vehicle getting stuck as well as the risk of the vehicle damaging the soil.

This ground bearing capacity mapping 21 can in the future be used for navigating autonomous vehicles over a field. Currently, operators visually control the status of the field to avoid getting stuck and to avoid damaging the soil. Using the ground bearing capacity mapping 21, this can be automated. At least, an operator is assisted in controlling the status of the field to avoid getting stuck and to avoid damaging the soil.

Based on the figures and the description, the skilled person will be able to understand the operation and advantages of the invention as well as different embodiments thereof. It is however noted that the description and figures are merely intended for understanding the invention, and not for limiting the invention to certain embodiments or examples used therein. Therefore it is emphasized that the scope of the invention will only be defined in the claims.

The invention claimed is:

1. A combine harvester comprising:
a header;
a controller;
a first sensor adapted to measure a first parameter indicating soil deformation and output a first output to the controller; and
a second sensor adapted to measure a second parameter indicating wheel slip and output a second output to the controller,
wherein the controller is configured to:
receive the first output and the second output; and
determine a ground bearing capacity based on a combination of the first output and the second output, and
wherein the header comprises at least one further sensor adapted to measure a further parameter related to the ground bearing capacity, the further sensor adapted to provide a further output to the controller.

2. The combine harvester according to claim 1, further comprising a ground drivability module, at least partially incorporating the controller, wherein the ground drivability module is configured to determine combine driving parameters based on the ground bearing capacity determined by the controller.

3. The combine harvester according to claim 2, wherein the ground drivability module is further configured to:
predict the ground bearing capacity of ground in front of the combine harvester, and
stop the combine harvester when the ground in front of the combine harvester is not able to carry the combine harvester.

4. The combine harvester according to claim 1, wherein the at least one further sensor comprises multiple sensors distributed over a width of the header at intermitting distances.

5. The combine harvester according to claim 1, wherein the controller is further configured to recursively calibrate the at least one further sensor based on the output of the first sensor or second sensor, respectively, so as to obtain an estimated ground bearing capacity for ground under the header.

6. The combine harvester according to claim 5, further comprising a ground drivability module, at least partially incorporating the controller, wherein the ground drivability module is configured to determine combine driving parameters based on the ground bearing capacity determined by the controller, wherein the ground drivability module is further configured to adapt the combine driving parameters based on the estimated ground bearing capacity.

7. The combine harvester according to claim 1, wherein the at least one further sensor is a soil density sensor, a soil humidity sensor, or a soil conductivity sensor.

8. The combine harvester according to claim 1, further comprising a third sensor adapted to measure a third parameter, the third parameter indicating a geographical position of the combine, the third sensor adapted to provide the third parameter to the controller, the controller further configured to relate the third parameter to the determined ground bearing capacity so as to obtain a ground bearing capacity mapping.

9. The combine harvester according to claim 8, wherein the ground bearing capacity mapping is broadcasted to agricultural vehicles in a proximity of the combine thereby allowing the agricultural vehicles to adapt their driving parameters based on the ground bearing capacity mapping.

10. The combine harvester according to claim 1, wherein the second sensor is a wheel slip sensor.

11. A combine harvester comprising:
a controller;
a first sensor adapted to measure a first parameter indicating soil deformation and output a first output to the controller; and
a second sensor adapted to measure a second parameter indicating wheel slip and output a second output to the controller,
wherein the controller is configured to:
receive the first output and the second output; and
determine a ground bearing capacity based on a combination of the first output and the second output, and
wherein the first sensor is a header position sensor, a driving power sensor, or a pair of soil density sensors, wherein a first one of the pair is arranged in front of a wheel and a second one of the pair is arranged behind the wheel.

* * * * *